United States Patent [19]
Khau et al.

[11] Patent Number: 5,461,156
[45] Date of Patent: Oct. 24, 1995

[54] STEREOCONTROLLED SYNTHESIS OF CIS-BICYCLIC COMPOUNDS

[75] Inventors: Vien V. Khau; Michael J. Martinelli; Barry C. Peterson; Kevin A. Sullivan, all of Indianapolis, Ind.

[73] Assignee: Eli Lilly and Company, Indianapolis, Ind.

[21] Appl. No.: 41,024

[22] Filed: Mar. 31, 1993

[51] Int. Cl.⁶ ............ C07D 217/04; C07D 217/06
[52] U.S. Cl. ............................................ 546/150
[58] Field of Search ................................ 546/150

[56] References Cited

U.S. PATENT DOCUMENTS 3,953,434  4/1976  Hauck ................................ 546/150

OTHER PUBLICATIONS

Uskokovic' et al., *Helvetica Chimica Acta*, 56, 2834–44(1973).

*Primary Examiner*—C. Warren Ivy
*Assistant Examiner*—D. Margaret M. Mach
*Attorney, Agent, or Firm*—Martin A. Hay; James P. Leeds

[57] ABSTRACT

This invention provides a process for the stereocontrolled synthesis of cis-bicyclic compounds, including cis-hexahydro-6-isoquinolones, cis-dihydroisochromanones, cis-dihydrothiochromanones, and cisbicyclo[ 4.4.0]dec-3-ene-2-ones.

7 Claims, No Drawings

STEREOCONTROLLED SYNTHESIS OF CIS-BICYCLIC COMPOUNDS

BACKGROUND OF THE INVENTION

Stereoselective and stereospecific routes for the synthesis of pharmaceutically-active compounds are continually in demand. The pharmaceutical activity of a particular chemical compound often resides in one isomer. See Laird, Chem. Ind (London), 366 (1989); Powel, Ambre, and Ruo, *Drug Chemistry*, 245–270 (1988); Borman, Chem, Eng. News, 68, 9 (Jul. 9, 1990); and Camp, Chirality, 1, 2 (1989). An efficient synthesis of the active isomer, therefore, requires a route that is stereoselective or stereospecific.

Natural products are frequently used in the synthesis of pharmaceutically-active compounds. Hanessian, *Total Synthesis of Natural Product: The "Chiron" Approach*, ix (1983); *Asymmetric Synthesis*, Vol. 4, Chapter 1 (1984); and Coppola and Schuster, *Asymmetric Synthesis* (1980). Generally, natural products have a defined stereochemical configuration that can be used in the synthesis of complex compounds, or that can be used to influence the stereochemical outcome of synthetic transformations. *Morrison and Mosher, Asymmetric Organic Reactions* (1976).

One group of natural products that have demonstrated a utility in organic synthesis is the cinchona alkaloids. This group includes such compounds as quinine, quinidine, cinchonidine, and cinchonine. Uskokovic et al. has described a process for the conversion of cinchonine into a 1:2.4 mixture of cis and trans-hexahydroisoquinolones, respectively. Uskokovic et al., Helv. Chim. Acta, 56, 2834–2844 (1973). This mixture of cis and trans isomers was separated and reduced to prepare optically pure (4aS,8aR) and (4aS, 8aS)-octahydroisoquinolones. A stereospecific or a more stereoselective route for the synthesis of hexahydroisoquinolones would be useful for the synthesis of pharmaceutically-active compounds.

A recent report shows that a series of 6-substituted decahydroisoquinoline-3-carboxylic acids act as competitive NMDA receptor antagonists and are suitable for use as neuroprotective agents in a variety of acute and chronic neurodegenerative disorders. Ornstein et al., *J. Med. Chem.*, 35, 3547–3560 (1992). One compound from this series, (±)-(3SR,4aRS, 6SR,8aRS)-6 -(phosphonomethyl)-decahydroisoquinoline-3-carboxylic acid, is a very potent and selective neuroprotective agent against excessive NMDA receptor activation in vivo in rats and in mice. Schoepp, Ornstein, Salhoff, and Leander, J. Neural Transm., 85, 131–143 (1991). This compound effectively blocks NMDA-induced convulsions in neonatal rats. This compound also provides neuroprotection against NMDA receptor-induced lethality in mature mice and rats. Surprisingly, the 3S isomer of this compound is active as an NMDA receptor antagonist, while the 3R isomer is inactive. Ornstein & Klimkowski, *Excitatory Amino Acid Receptors: Design of Agonists and Antagonists*, 183–200 (1992). This agent, as well as other compounds in the series, may prove therapeutically useful in treating acute pathological conditions that involve glutamate excitotoxicity. Therefore, an efficient stereocontrolled synthesis of these compounds is desired.

SUMMARY OF THE INVENTION

The present invention relates to a process for the stereocontrolled synthesis of cis-bicyclic compounds. In particular, the present invention provides a process for the stereocontrolled synthesis of cis-hexahydroisoquinolones, cis-dihydroisochromanones, cis-dihydroisothiochromanones, and cis-bicyclo[4.4.0]dec-3-ene- 2-ones. These compounds are useful in the synthesis of pharmaceutically-active compounds, such as NMDA receptor antagonists (±)-(3SR, 4aRS, 6SR,8aRS)-6 -(phosphonomethyl)-decahydroisoquinoline-3-carboxylic acid and steroidal isosteres. More specifically, the present invention relates to a process for preparing a compound of the formula

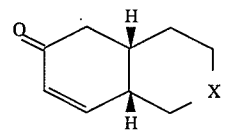

wherein

X is $NR^1$, S, O, or $CH_2$; and $R^1$ is hydrogen, $C_1-C_6$ alkyl, arylalkyl, acyl, $C_1-C_6$ alkylsulfonyl, arylsulfonyl, alkoxycarbonyl, aryloxycarbonyl, or arylalkoxycarbonyl;

which comprises reacting a compound of the formula

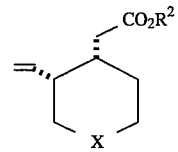

wherein x is as defined above; and $R^2$ is hydrogen, t-butyl, $(C_1-C_6$ alkyl$)_3$silyl, methoxyethoxymethyi, methoxymethyl, tetrahydrofuran-2-yl, tetrahydropyran-2-yl, arylalkyl, cinnamyl, or allyl; with sulfuric acid.

DETAILED DESCRIPTION OF THE INVENTION

The term "$C_1-C_6$ alkyl" represents a straight or branched alkyl chain having from one to six carbon atoms. Typical $C_1-C_6$ alkyl groups include methyl, ethyl, n-propyl, isopropyl, n-butyl, isobutyl, sec-butyl, t-butyl, n-pentyl, isopentyl, and n-hexyl. The term "$C_1-C_6$ alkyl" includes within it the term "$C_1-C_4$ alkyl". Typical $C_1-C_4$ alkyl groups include methyl, ethyl, n-propyl, isopropyl, n-butyl, isobutyl, sec-butyl, and t-butyl.

The term "$C_1-C_4$ alkoxy" represents groups such as methoxy, ethoxy, n-propoxy, isopropoxy, n-butoxy, t-butoxy, and like groups. The term "halogen" refers to the fluoro, chloro, bromo, or iodo groups.

The term "substituted phenyl," as used herein, represents a phenyl group substituted with one or two moieties chosen from the group consisting of halogen, hydroxy, cyano, nitro, $C_1-C_6$ alkyl, $C_1-C_4$ alkoxy, alkoxycarbonyl, carboxymethyl, hydroxymethyl, amino, aminomethyl, and trifluoromethyl. Examples of a substituted phenyl group include 4-chlorophenyl, 2,6 -dichlorophenyl, 2,5-dichlorophenyl, 3,4-dichlorophenyl, 3 -chlorophenyl, 3-bromophenyl, 4-bromophenyl, 3,4 -dibromophenyl, 3-chloro-4-fluorophenyl, 2-fluorophenyl, 4 -hydroxyphenyl, 3-hydroxyphenyl, 2,4-dihydroxyphenyl, 3 -nitrophenyl, 4-nitrophenyl, 4-cyanophenyl, 4-methylphenyl, 3,4-dimethylphenyl, 4-ethylphenyl, 4-methoxyphenyl, 4 -carboxyphenyl, 4-(hydroxymethyl)phenyl, 4-aminophenyl, 4 -(methoxycarbonyl) phenyl, 4-trifluoromethylphenyl, and the like.

The term "aryl" represents groups such as phenyl and substituted phenyl as described above. The term "arylalkyl" represents a $C_1$–$C_4$ alkyl group bearing an aryl group. Representatives of this latter group include benzyl, 1-phenylethyl, 2-phenylethyl, 3-phenylpropyl, 4-phenylbutyl, 2-methyl-2-phenylpropyl, (4-chlorophenyl)methyl, (2,6-dichlorophenyl)methyl, (4-hydroxyphenyl)methyl, (2,4-dinitrophenyl)methyl, and the like.

The term "acyl" represents a hydrogen, $C_1$–$C_6$ alkyl group, or aryl group attached to a carbonyl group. Typical acyl groups include formyl, acetyl, propionyl, butyryl, valeryl, pivaloyl, caproyl, benzoyl, 4-nitrobenzoyl, and the like.

The term "alkoxycarbonyl" means a carboxyl group having a $C_1$–$C_6$ alkyl group attached to the carbonyl carbon through an oxygen atom. Representatives of this group include t-butoxycarbonyl and methoxycarbonyl.

The term "aryloxycarbonyl" represents a carboxyl group bearing an aryl group attached to the carbonyl carbon through an oxygen atom. Representatives of this group include phenoxycarbonyl, (4-chlorophenoxy)carbonyl, and (3-nitrophenoxy)carbonyl.

The term "arylalkoxycarbonyl" represents a carboxyl group having an arylalkyl group attached to the carbonyl carbon through an oxygen atom. Representatives of this group include benzyloxycarbonyl, 2-phenylethoxycarbonyl, 3-phenylpropoxycarbonyl, and the like. The preferred arylalkoxycarbonyl group is benzyloxycarbonyl.

The term "$C_1$–$C_6$ alkylsulfonyl" means a sulfonyl ($SO_2$) group having a $C_1$–$C_6$ alkyl group attached to the sulfur atom. Representatives of this group include methanesulfonyl, ethanesulfonyl, n-propanesulfonyl, i-propanesulfonyl, n-butanesulfonyl, and t-butanesulfonyl. Similarly, the term "arylsulfonyl" means a sulfonyl group having an aryl group attached to the sulfur atom. Representatives of this group include benzenesulfonyl, toluenesulfonyl, and the like.

The term "$(C_1$–$C_6$ alkyl$)_3$silyl" represents a silicon atom having three $C_1$–$C_6$ alkyl groups, which may be the same or different. Representatives of this group include trimethylsilyl, triethylsilyl, t-butyldimethylsilyl, and the like.

While all the formula II compounds of the present invention are believed to be useful in the synthesis of the formula I compounds, certain compounds of the invention are preferred for such use. Preferably, X is $NR^1$, $R^1$ is hydrogen, $C_1$–$C_6$ alkyl, arylalkyl, acyl, arylsulfonyl, alkoxycarbonyl, or arylalkoxycarbonyl, and $R^2$ is hydrogen, t-butyl, $(C_1$–$C_6$ alkyl$)_3$silyl, methoxyethoxymethyl, methoxymethyl, or tetrahydropyran-2-yl. Examples of this preferred group of compounds includes meroquinene, meroquinene t-butyl ester, meroquinene trimethylsilyl ester, meroquinene methoxyethoxymethyl ester, meroquinene methoxymethyl ester, meroquinene tetrahydropyran-2-yl ester, 1-benzylmeroquinene, 1-benzylmeroquinene t-butyl ester, 1-benzylmeroquinene trimethylsilyl ester, 1-benzylmeroquinene methoxyethoxymethyl ester, 1-benzylmeroquinene methoxymethyl ester, 1-benzylmeroquinene tetrahydropyran-2-yl ester, 1-benzyloxycarbonylmeroquinene, 1-benzyloxycarbonylmeroquinene t-butyl ester, 1-benzyloxycarbonylmeroquinene trimethylsilyl ester, and 1-methoxycarbonylmeroquinene methoxyethoxymethyl ester.

More preferably, $R^1$ is $C_1$–$C_6$ alkyl, acyl, arylsulfonyl, or alkoxycarbonyl, and $R^2$ is hydrogen, butyl, $(C_1$–$C_6$ alkyl$)_3$silyl, or methoxymethyl. Examples of this more preferred group of compounds includes 1-methylmeroquinene, 1-methylmeroquinene t-butyl ester, 1-methylmeroquinene trimethylsilyl ester, 1-benzenesulfonylmeroquinene, 1-benzenesulfonylmeroquinene butyl ester, 1-benzenesulfonylmeroquinene trimethylsilyl ester, 1-methoxycarbonylmeroquinene trimethylsilyl ester, and 1-methoxycarbonylmeroquinene methoxymethyl ester.

Most preferably, $R^1$ is an acyl or alkoxycarbonyl group, and $R^2$ is hydrogen or t-butyl. Examples of this most preferred group of compounds includes 1-methoxycarbonylmeroquinene, 1-methoxycarbonylmeroquinene t-butyl ester, 1-acetylmeroquinene, and 1-acetylmeroquinene t-butyl ester. The most preferred formula II compound for use in the process of the present invention for preparing the formula I compound is the compound wherein X is $NR^1$, $R^1$ is methoxycarbonyl and $R^2$ is t-butyl.

The formula I compounds possess two asymmetric carbon atoms. These asymmetric centers are the two bridgehead carbon atoms (4a and 8a). The formula II compounds also possess two asymmetric carbon atoms. These asymmetric centers are the substituted carbon atom where the ethylene group is attached to the ring (3) and the carbon atom where the carboxymethyl group is attached to the ring (4). In the present process, the stereochemistry of the formula II compounds is preserved in the cyclization to form the formula I compounds. The C-3 and C-4 stereocenters of the formula II compounds correspond to the C-8a and C-4a stereo centers of the formula I compounds, respectively.

The configuration for the preferred enantiomer of the formula I compound is 4aS, 8aS. The relative and absolute stereochemistry for this preferred enantiomer is shown in the following formula.

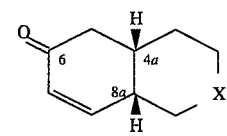

The formula II compounds, wherein X is $NR^1$, are prepared as outlined in Scheme I.

Scheme I

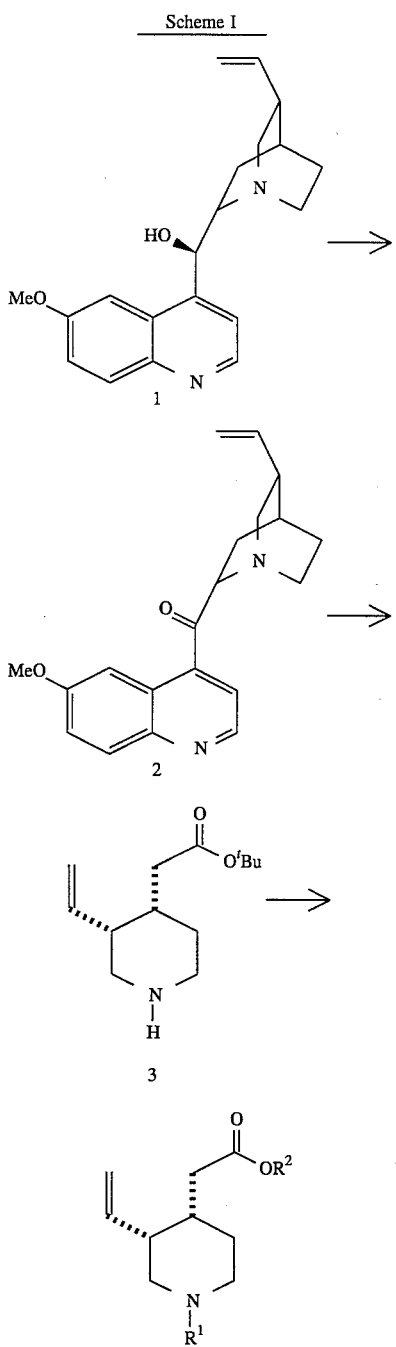

Generally, the naturally occurring alkaloid quinine (1) is oxidized to quininone (2). This compound is then further oxidized, employing a modification to the Uskokovic procedure, to produce meroquinene t-butyl ester (3). Uskokovic et al., Helv. Chim. Acta, 56, 2834–2844 (1973). The ring nitrogen may be protected and the ester group exchanged for another acid-sensitive group to produce the formula II compound.

More specifically, quinine (1) is oxidized to quininone (2) by a variety of standard oxidizing agents. Such oxidizing agents include the Jones reagent ($H_2CrO_4$/acetone), the Swern reagent, or other DMSO-based oxidizing agents. Hudlicky, Oxidations in Organic Chemistry, ACS Monograph 186, 21–22 (1990); Mancuso, Huang, and Swern, J. Org. Chem., 43, 2480 (1978); and Epstein & Sweat, Chem. Rev., 67, 247 (1967). The preferred oxidizing agent for this transformation is the combination of benzophenone and potassium t-butoxide as described by Woodward. Woodward, Wendler, and Brutschy, J. Am. Chem. Soc., 67, 1425 (1945). This oxidation is carried out in an organic solvent, such as toluene or benzene, at the reflux temperature of the solvent. When the solvent is toluene, the reaction is typically complete after about 18 hours.

Meroquinene t-butyl ester is prepared by auto-oxidation of quininone (2). This autoxidation is carried out in the presence of potassium t-butoxide in an organic solvent. Suitable organic solvents include alcoholic solvents, such as methanol, ethanol, n-butanol, and t-butanol, or a mixture of an organic solvent, such as tetrahydrofuran, and an alcoholic solvent. The preferred solvent for this oxidation is a mixture of tetrahydrofuran and t-butanol (2:1). When an alcohol other than t-butanol is employed as the solvent, the product of the reaction will be the ester corresponding to the alcohol used as a solvent. The reaction is generally carried out at a temperature of about 0° C. to about 30° C., preferably less than 25° C., in the presence of oxygen gas. Preferably, the solution is saturated with oxygen gas by means of a continuous oxygen gas purge. Preferably, solid quininone is added to the potassium t-butoxide solution at a rate to maintain the temperature of the reaction solution below 30° C.

The meroquinene ester (3) is preferably protected on the ring nitrogen. Methods for the protection of amino groups are generally described in Greene and Wutz, Protective Groups in Organic Synthesis, 309–385 (2d ed., 1991) and McOmie, Protective Groups in Organic Chemistry, 43–74 (1973). The amino group may be protected with a $C_1$–$C_6$ alkyl, arylalkyl, acyl, $C_1$–$C_6$ alkylsulfonyl, arylsulfonyl, alkoxycarbonyl, aryloxycarbonyl, or arylalkoxycarbonyl group. The preferred amino protecting groups are $C_1$–$C_6$ alkyl, arylalkyl, acyl, arylsulfonyl, alkoxycarbonyl, or arylalkoxycarbonyl groups. More preferably, the amino protecting group is a $C_1$–$C_6$ alkyl, acyl, arylsulfonyl, or alkoxycarbonyl group. The most preferred amino protecting groups are the acyl and alkoxycarbonyl group. The methoxycarbonyl group is especially preferred.

The methoxycarbonyl substituted meroquinene t-butyl ester is prepared using standard synthetic organic techniques. Meroquinene t-butyl ester (3) is reacted with methyl chloroformate in the presence of an amine base or an inorganic base. Suitable amine bases for this transformation include N,N-diisopropylethylamine, pyridine, triethylamine, N-methylmorpholine, and the like. Suitable inorganic bases include sodium bicarbonate, sodium carbonate, and potassium carbonate. This reaction preferably is carried out at a temperature of about 0° C. to about 15° C. for a period of about two hours.

The t-butyl ester group may be removed and optionally replaced with another acid-sensitive group. Methods for the hydrolysis of t-butyl esters and subsequent protection of the carboxyl group are generally described in Greene and Wutz, Protective Groups in Organic Synthesis, 224–263 (2d ed., 1991) and McOmie, Protective Groups in Organic Chemistry, 183–210 (1973). The carboxyl group may be protected as the t-butyl, ($C_1$–$C_6$ alkyl)$_3$silyl, methoxyethoxymethyl, methoxymethyl, tetrahydrofuran-2-yl, tetrahydropyran-2-yl, arylalkyl, cinnamyl, or allyl ester. These esters are prepared using standard synthetic organic techniques as described in the above references. The preferred acid-sensitive carboxyl groups are t-butyl, ($C_1$–$C_6$ alkyl)$_3$silyl, methoxyethoxymethyl, methoxymethyl, or tetrahydropyran-2-yl. More preferably, the carboxyl group is a t-butyl, $(C_1-C_6\text{ alkyl})_3$silyl, or methoxymethyl ester. Most preferably, the acid-sensitive carboxyl group is a t-butyl group.

The formula II compounds, wherein X is $CH_2$, O, or S, are prepared as shown in Scheme II.

Scheme II

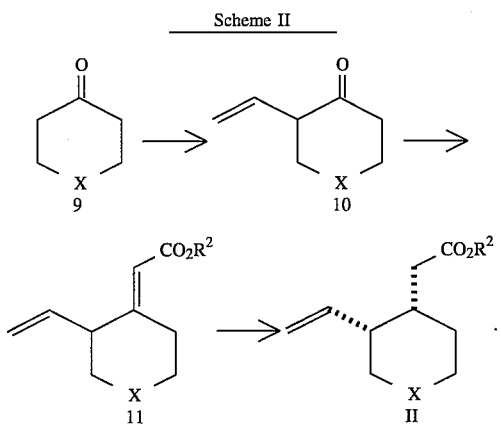

Generally, the cyclic ketone (9) is alkylated or condensed with an ethylene group precursor. This precursor is then converted to an ethylene group to prepare the unsaturated intermediate (10). This intermediate is reacted with a Horner-Emmons reagent to produce the unsaturated ester (11). The exocyclic double bond is stereoselectively reduced to prepare the formula II compound.

More specifically, a cyclic ketone, such as cyclohexanone, tetrahydro-4H-pyran-4-one, or tetrahydrothiopyran-4-one, is treated with a strong base and alkylated or condensed with an ethylene group precursor. Suitable strong bases for this transformation include lithium diisopropylamide and sodium bis(trimethylsilyl)amide. The solvent for this transformation is typically an anhydrous organic solvent, such as dry tetrahydrofuran. Examples of alkylating reagents that can readily be converted to an ethylene group include ethylene oxide and 1,2-dibromoethane. The products of the alkylation reaction are then dehydrated or dehydrohalogenated using standard synthetic organic techniques. An example of a condensing reagent that can be readily converted to an ethylene group is $PhSeCH_2CHO$. This condensation product is treated with methanesulfonyl chloride and triethylamine to produce the ethylene group.

Unsaturated intermediate 10 is condensed with a Horner-Emmons reagent to produce intermediate 11. The Horner-Emmons reagent has the general formula $(CH_3CH_2O)_2POCH_2CO_2R^2$, wherein $R^2$ is as defined previously. The reaction is generally accomplished by treating the diethyl phosphonate (Horner-Emmons reagent) with a strong base, such as sodium hydride, to generate the sodium salt of the diethyl phosphonate. This salt is then reacted with intermediate 10 in an organic solvent, such as dry tetrahydrofuran. The reaction is typically carried out at a temperature of about 0° C. to about 25° C., preferably at about 25° C. The reaction is generally complete after a period of about two hours.

Unsaturated intermediate 11 is reduced to prepare a compound of formula II. This reduction requires a stereoselective reducing agent in order to maximize the yield of the desired product. A suitable reducing agent for this transformation is $[Ph_3PCuH]_6$. Bretensky et al, Tetr. Lett., 29, 3749–52 (1988); and Mahoney, Brestensky, and Stryker, J. Am. Chem. Soc., 110, 291–93 (1988). This reduction is carried out in an organic solvent, such as benzene or toluene, under an inert atmosphere ($N_2$) at room temperature.

The formula I compounds are prepared from the formula II compounds as outlined in Scheme Ill.

Scheme III

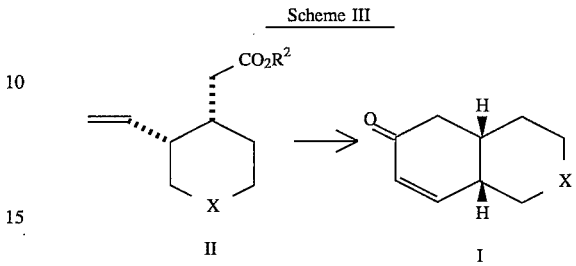

Generally, the formula I compound is produced by sulfuric acid-catalyzed cyclization of the formula II compound. More specifically, the formula II compound is cyclized to stereospecifically produce a cis-bicyclic compound of formula I, cis-hexahydroisoquinolones, cis-dihydroisochromanones, cis-dihydroisothiochromanones, or cis-bicyclo [4.4.0]dec-3-ene-2-ones. The preferred acid catalyst for the cyclization is concentrated sulfuric acid. The reaction may be carried out using sulfuric acid as the solvent, or using a mixture of sulfuric acid and polyphosphoric acid as the solvent. Preferably, the reaction is carried out in concentrated sulfuric acid. The reaction is also carried out at a temperature of about 0° C. to about 20° C. This cyclization is typically complete after a period of about two hours.

The sulfuric acid-catalyzed cyclization of the formula II compounds produces only the formula I compounds having cis substitution at the bridgehead. To illustrate the stereocontrol of %he present process, a number of formula II compounds, wherein X is $NR^1$, were converted to the corresponding formula I compounds. The results of these experiments are shown in the Table.

TABLE

Sulfuric Acid Catalyzed Cyclization of Formula II Compounds.

| $R^1$ | $R^2$ | Yield (%) |
|---|---|---|
| CoPh | t-Bu | 98% |
| $CO_2CH_3$ | t-Bu | 85–99%[b] |
| $CO_2CH_2Ph$ | t-Bu | 80%[a] |
| $COCH_3$ | t-Bu | 65% |
| COt-Bu | t-Bu | 80%[c] |
| p-Tos | t-Bu | 70% |
| CoPh | H | 30% |
| $CO_2CH_3$ | H | 85–90%[b] |

[a]Average yield of two experiments
[b]Range of yields for multiple experiments
[c]Yield calculated after chromatographic purification The formula I compounds, wherein X is $NR^1$, are useful as starting materials for the synthesis of 6-substituted decahydroisoquinoline-3-carboxylic acids as shown in Scheme IV. The formula III compounds are useful as neuroprotective agent. See Ornstein et al, J. Med. Chem., 35, 3547–50 (1992).

Scheme IV

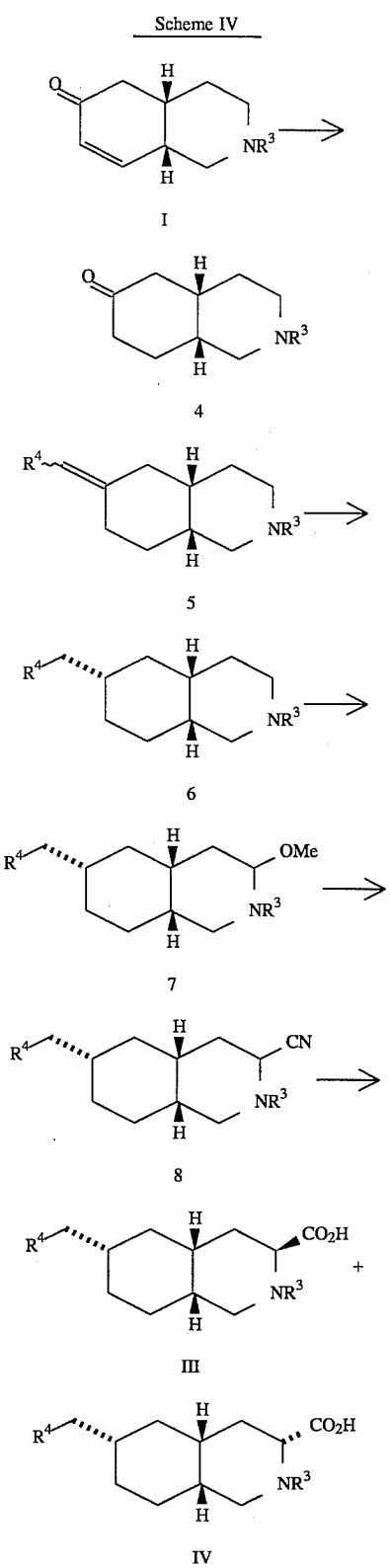

Generally, the formula I compound is selectively reduced to prepare intermediate 4, wherein $R^3$ is hydrogen, $C_1$–$C_6$ alkyl, arylalkyl, acyl, $C_1$–$C_6$ alkylsulfonyl, arylsulfonyl, alkoxycarbonyl, aryloxycarbonyl, or arylalkoxycarbonyl. This intermediate is then condensed with a Wittig reagent or a Horner-Emmons reagent to produce intermediate 5. This condensation product is then stereoselectively reduced to intermediate 6. This compound is oxidized to intermediate 7, which is cyanated to prepare intermediate 8. This compound is hydrolyzed to a mixture of C-3 epimers, formula III and formula IV. This mixture of C-3 epimers may be treated with a strong base to epimerize the C-3 stereocenter.

More specifically, the formula I compounds, wherein X is $NR^1$, are selectively reduced to prepare the intermediate cis-decahydroisoquinol-6-ones (4). The preferred method of reduction is catalytic hydrogenation. Suitable hydrogenation catalysts include 10% palladium on carbon, 10% platinum on carbon, and platinum oxide. The preferred catalyst for this hydrogenation is 10% palladium on carbon. The reaction is typically carried out in an organic solvent, such as ethyl acetate or ethanol. The preferred solvent is ethanol. The reduction is preferably carried out at a hydrogen pressure of about 15 psi and at a temperature of about 20° C. to about 30° C. The reaction is typically complete after about two hours.

Intermediate 4 is reacted with a Horner-Emmons reagent or a Wittig reagent to prepare the formula VII compounds. The Horner-Emmons reagent has a general formula $(R^5O)_2POCH_2R^4$, wherein $R^4$ is $CO_2R^5$, $CON(R^5)_2$, $PO(OR^5)_2$,

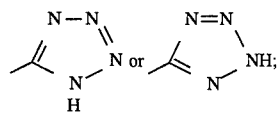

and $R^5$ is $C_1$–$C_6$ alkyl or arylalkyl. This Wittig reagent has the general formula $Ph_3PCH_2R^4$, wherein $R^4$ is as defined previously. The Horner-Emmons reagent is preferred for use in this reaction. The reaction is generally accomplished by treating the appropriate diethyl phosphonate (Horner-Emmons reagent) or Wittig reagent with a strong base, such as sodium hydride, to generate the sodium salt of the phosphonate or the ylid. This salt or ylid is then reacted in an organic solvent, such as dry tetrahydrofuran, to provide intermediate 5. The reaction is typically carried out at a temperature between 0° C. and 70° C., preferably at 70° C. The reaction is generally complete after about 30 minutes to about four hours.

Intermediate 5 is stereoselectively reduced to intermediate 6. A preferred method for this stereoselective reduction is catalytic hydrogenation, preferably in the presence of 10% palladium on carbon in an inert solvent. Suitable inert solvents include ethanol and ethyl acetate, preferably ethanol. This stereoselective reduction is typically carried out at a temperature of about 25° C. to about 40° C., and at a hydrogen pressure of about 15 psi. The reaction is typically complete after of a period of about eight to about sixteen hours.

Intermediate 6 is oxidized to intermediate 7. The preferred method for this oxidation is anodic oxidation. Generally, a current is applied to carbon plate electrodes immersed into a solution containing intermediate 6 and an electrolyte, such as tetraethylammonium p-toluenesulfonate, in an organic solvent, such as methanol. This anodic oxidation produces a mixture of regioisomer, having a methoxy group at C-1 and C-3, and diastereomers, which differ in the C-1 and C-3 stereochemical configuration. This mixture of isomers is preferably used in the subsequent steps without separation.

Intermediate 7 is cyanated to produce intermediate 8. Generally, intermediate 7 is reacted with trimethylsilyl cyanide in the presence of a Lewis acid in an organic solvent, such as methylene chloride. Suitable Lewis acids include tin(IV) chloride, boron trifluoride etherate, and aluminum chloride; tin(IV) chloride is preferred. Generally, trimethylsilyl cyanide is treated with the Lewis acid at a temperature of about 20° C., then cooled to a temperature of about −60° C. and treated with the solution of intermediate 7 in an organic solvent. The cooled solution is then allowed to warm to a temperature of about −30° C., and the reaction is quenched by the addition of aqueous base.

Intermediate 8 is hydrolyzed to produce a mixture containing the formula III compound and its C-3 epimer, the formula IV compound. This hydrolysis is carried out in the presence of an aqueous acid, such as hydrochloric acid and polyphosphoric acid, or a strong organic acid, such as trifluoroacetic acid. The preferred acid for the hydrolysis is concentrated hydrochloric acid. The reaction is typically carried out at a temperature of about 50° C. to about 100° C., preferably at about 80° C. This hydrolysis is typically complete after a period of about 24 hours to about 30 hours. The diastereomeric products, the formula III compound and the formula IV compound, may be separated using standard chromatographic techniques, such as high performance liquid chromatography. Preferably, the mixture of isomers is used in the next step.

The mixture containing C-3 epimers may be treated with a strong base to equilibrate the mixture in favor of the formula III compounds. Suitable strong bases for this equilibration include sodium hydroxide, potassium hydroxide, and a combination of sodium methoxide in methanol. The preferred base for equilibration is 40% potassium hydroxide. When the equilibration is carried out at the reflux temperature of the reaction mixture, the reaction is typically complete after a period of about two and one-half days.

The following examples further illustrate the compounds and the processes of the present invention. The examples are not intended to be limiting to the scope of the invention in any respect, and should not be so construed. Proton nuclear magnetic resonance ($^1$H NMR) spectra were recorded on a GE QE-300 spectrometer at 300.15 MHz. Carbon nuclear magnetic resonance ($^{13}$C NMR) spectra were recorded on a GE QE-300 spectrometer at 75.0 MHz. The reactions were generally monitored for completion using thin layer chromatography (TLC). Thin layer chromatography was generally performed using E. Merck Kieselgel 60 $F_{254}$ plates, 5 cm×10 cm, 0.25 mm silica gel thickness. Silica-gel flash chromatography was performed as described by Still et al. Still, Kahn, and Mitra, J. Org. Chem., 43, 2923 (1978).

Preparation 1

Preparation of Quininone

A solution of benzophenone (1.12 kg) in toluene (4 L) was treated with quinine (1.00 kg) and potassium t-butoxide (871 g). The resulting mixture was heated to reflux for six hours, then allowed to cool to room temperature. After about 18 hours, this mixture was cooled to a temperature of about 10° C. to about 15° C. This cold mixture was treated with 2N hydrochloric acid (4 L) at a rate such that the temperature of the mixture was less than 30° C. The resulting mixture was treated with additional 2N hydrochloric acid (3 L) and the phases separated. The organic phase was extracted with additional 2N hydrochloric acid (2×2.5 L). The combined aqueous phase was cooled to a temperature of about 5° C. to about 15° C., and the pH adjusted to pH 9–9.5 with the addition of 5N sodium hydroxide (ca. 2.6 L). The resulting mixture was stirred am about 5° C. to about 20° C. for one hour. The crystalline material was removed by filtration, rinsed with water (2×1L), and dried in vacuo at 50° C. to give 1.02 kg of quininone.

Preparation 2

Preparation of Meroquinene t-Butyl Ester

A mixture of tetrahydrofuran (200 ml) and t-butanol (100 ml) was added to potassium t-butoxide (43.50 g). The resulting solution was cooled to 4° C. and treated with oxygen gas. This cold solution was treated with a solution of quininone (50 g) in tetrahydrofuran (200 ml) and the rate of oxygen addition was adjusted to maintain the temperature of the solution below 30° C. After the red color had dissipated, the addition of oxygen gas was continued for another five minutes and the temperature of the solution was maintained above 20° C. This mixture was vigorously stirred at 20° C. and treated with acetic acid (40 ml). The resulting slurry was concentrated in vacuo and the residue dissolved in water (20 ml). The pH of the solution was adjusted to pH 9–10 by the addition of concentrated ammonium hydroxide (25 ml). The resulting solution was extracted with ether (4×110 ml). The combined organic extracts were dried over magnesium sulfate, and concentrated in vacuo to give 24.04 g of meroquinene t-butyl ester as a viscous oil.

Preparation 3

Preparation of 1-Methoxycarbonylmeroquinene t-Butyl Ester

A solution of meroquinene t-butyl ester (5.15 g) and N,N-diisopropylethylamine (5.98 ml) in methylene chloride (36 ml) was cooled to about 0° C. to about 5° C. This cold solution was treated with methyl chloroformate (2.12 ml) at a rate to maintain the temperature below 15° C. The resulting solution was allowed to warm to room temperature and extracted with 1N hydrochloric acid. The organic phase was extracted with dilute sodium bicarbonate, dried over sodium sulfate, and concentrated in vacuo to give 5.53 g of the title compound as a brown oil.

$^1$H NMR (CDCl$_3$): δ5.71–5.83 (m, 1H); 5.06–5.16 (m, 2H); 3.92–4.11 (m, 2H); 3.86 (s, 3H); 3.08 (dd, 1H); 2.92 (m, 1H); 2.37–2.39 (m, 1H); 2.03–2.23 (m, 3H); 1.44 (s, 9H); 1.37–1.57 (m, 2H).

$^{13}$C NMR (CDCl$_3$): δ 171.7, 156.1, 135.1, 117.4, 80.1, 52.4, 48.1, 43.5, 42.1, 38.7, 35.5, 28.0, 27.2.

EXAMPLE 1

Preparation of (4aS,8aS)-2-Methoxycarbonylhexahydro-6-isoquinolone

Concentrated sulfuric acid (19 ml) was cooled to −25° C. and treated with the compound from Preparation 3 (4.71 g). The resulting solution was stirred at 0° C. for 30 minutes and at 20° C. for 1½ hours. This solution was added to ice (64 g), and the resulting mixture extracted with methylene chloride (4×20 ml). The organic extracts were combined and concentrated in vacuo to a residue. The residue was purified by silica-gel flash chromatography, eluting with 20% ethyl acetate/methylene chloride to give 2.95 g of the title compound.

$^1$H NMR (CDCl$_3$): δ6.79–6.82 (m, 1H); 6.05 (dd, 1H); 3.76–3.94 (m, 2H); 3.70 (s, 3H); 3.36 (dd, 1H); 3.09–3.17 (m, 1H); 2.73 (m, 1H); 2.39–2.56 (cm, 3H); 1.56–1.63 (m, 2H).

$^{13}$C NMR (CDCl$_3$): δ197.8, 155.4, 150.2, 130.4, 52.2, 46.2, 41.9, 41.4, 36.2, 33.2, 26.2.

Preparation 4

Preparation of (4aS, 8aR)-2-Methoxycarbonyloctahydro-6-isoquinolone

A mixture of the compound from Example 1 (2.29 g) and 16% palladium on carbon (0.23 g) in ethanol (23 ml) was hydrogenated using a hydrogen pressure of 20 psi at ambient temperature. After 2 hours, the catalyst was removed by filtration and the filtrate concentrated in vacuo to give 2.26 g of the title compound as an oil.

$^1$H NMR (CDCl$_3$): δ3.92–3.99 (m, 2H); 3.67 (s, 3H); 3.11–3.55 (m, 1H); 2.85–2.95 (m, 1H); 2.53–2.60 (m, 1H); 2.12–2.42 (m, 5H); 1.90–2.03 (m, 2H); 1.46–1.52 (m, 2H).

$^{13}$C NMR (CDCl$_3$): δ209.6, 155.4, 51.7, 46.6, 45.2, 42.6, 39.0, 36.3, 33.7, 26.1, 24.6.

Preparation 5

Preparation of (4aR,8aR)-6-(Diethyl phosphonomethylene)-2-methoxycarbonyldecahydroisoquinoline A mixture of sodium hydride (0.61 g) in tetrahydrofuran (15 ml) was cooled and treated with tetraethyl methylenediphosphonate (6.36 ml). After three hours, the reaction mixture was treated with a solution of the compound from Preparation 4 (2.19 g) in tetrahydrofuran (15 ml). The resulting mixture was heated to reflux. After 2½ hours, the reaction solution was added to water (30 ml) and the resulting mixture extracted with ether (3×20 ml). The combined ether extracts were washed with 5N sodium hydroxide (2×15 ml) and with saturated sodium bicarbonate (15 ml), dried over magnesium sulfate, and concentrated in vacuo to give 4.76 g of the title compound as a oil.

$^1$H NMR (CDCl$_3$): δ5.29–5.44 (m, 1H); 3.99–4.11 (m, 6H); 3.79–3.98 (m, 2H); 3.66 (s, 3H); 3.14–3.18 (m, 1H); 3.00–3.05 (m, 1H); 2.86 (m, 1H); 1.87–2.48 (m, 5H); 1.29–1.37 (m, 6H); 1.25–1.78 (m, 4H).

$^{13}$C NMR (CDCl$_3$): δ162.5, 162.4, 155.7, 112.1, 112.0, 109.6, 109.5, 60.8, 60.7, 60.6, 51.9, 47.5, 47.4, 43.1, 42.9, 42.6, 37.1, 36.8, 36.0, 35.8, 35.3, 35.3, 35.2, 34.8, 34.7, 29.9, 29.8, 25.9, 25.6, 25.5, 25.4, 25.3, 15.8.

Preparation 6

Preparation of (4aR,6S, 8aR)-6-(Diethyl phosphonomethyl)-2-methoxycarbonyldecahydroisoquinoline A mixture of the compound from Preparation 5 (4.76 g) and 10% palladium on carbon (0.6 g) in ethanol (30 ml) was hydrogenated at 40° C. and a hydrogen pressure of 15 psi. After sixteen hours, the reaction mixture was added to methylene chloride (200 ml). This mixture was filtered through silica-gel, and the silica-gel washed with 20% ethanol/methylene chloride (250 ml). The flitrates were combined and concentrated in vacuo to a residue. The residue is purified by silica-gel chromatography, eluting with ethyl acetate, to give 4.52 g of the title compound.

$^1$H NMR (CDCl$_3$): δ4.03–4.14 (m, 6H); 3.70–4.00 (m, 2H); 3.67 (s, 3H); 2.79–2.98 (m, 2H); 1.29–1.91 (m, 8H); 1.01–1.13 (m, 1H).

$^{13}$C NMR (CDCl$_3$): δ155.4, 60.7, 60.6, 51.7, 42.5, 38.5, 33.5, 33:0, 32.4, 32.3, 32.2, 32.0, 31.7, 30.4, 28.5, 28.3, 15.9, 15.8.

Preparation 7

Preparation of (3SR, 4aR, 6S, 8aR) -3-Methoxy-2-methoxycarbonyl-6-phosphonomethyldecahydroisoquinoline Four carbon plate electrodes were immersed into a solution containing the compound from Preparation 6 (250 mg), tetraethylammonium p-toluenesulfonate (21 mg), in methanol (10 ml). A constant current of 0.5 A was applied to the electrodes. Additional methanol (7.8 ml) was added to the reaction to replace methanol which was lost due to evaporation. After 550 coulombs of current had passed, the electrodes were removed and the solution was added to 10% brine. This mixture was extracted with ether (3×15 ml). The combined ether extracts were washed with water and with brine, dried over magnesium sulfate, and concentrated in vacuo at room temperature to give 237 ml of the title compound as an oil. The material was stored in the refrigerator and used in the next step without further purification.

Preparation 8

Preparation of (3SR,4aR,6S, 8aR)-3-Cyano-2-methoxycarbonyl- 6-phosphonomethyldecahydroisoquinoline A solution of trimethylsilyl cyanide (10 ml) in methylene chloride (72 ml) was cooled to 20° C. and treated with tin(IV) chloride (8.8 ml) at a rate such that the temperature of the solution was less than 30° C. After the addition of the tin(IV) chloride was complete, the solution was cooled to –60° C. and treated with a solution of the compound from Preparation 7 (14.36 g) in methylene chloride (72 ml). After 20 minutes at –60° C., the solution was warmed to –30° C. over 10 minutes. This mixture was added to water and the phases separated. The aqueous phase was extracted with methylene chloride (50 ml). The organic phases were combined and treated with 50% caustic and with ethyl acetate. The organic phase was removed and the aqueous phase was extracted with ethyl acetate. The combined organic phases were washed with water and with brine, and concentrated in vacuo to give 13.17 g of the title compound as an oil.

Preparation 9

Preparation of (3SR, 4aR, 6S, 8aR) -6 -Phosphonomethyldecahydroisoquinoline-3-carboxylic acid A mixture of the compound from Preparation 8 (12.64 g) and concentrated hydrochloric acid (40 ml) was heated to reflux. After 26½ hours, the mixture was allowed to cool to 80° C. and treated with charcoal (2 g). This mixture was heated to reflux for 10 minutes, then the charcoal was removed by filtration. The solids were washed with water (60 ml). The filtrate and wash were combined and extracted with methylene chloride (2×20 ml) and with chloroform (1×20 ml), and concentrated in vacuo to a brown foam containing about 60% of the title compound.

Preparation 10

Preparation of (3S, 4aR,6S, 8aR)-6 -Phosphonomethyldecahydroisoquinoline-3-carboxylic acid The mixture from Preparation 9 (9.15 g) was added to 40% potassium hydroxide (45 ml). The resulting solution was heated to reflux. After 2½ days, the reaction mixture was allowed to cool to room temperature, neutralized with hydrochloric acid, and concentrated in vacuo to a brown oil. High performance liquid chromatographic (HPLC) analysis (WATERS NOVA C18 columnm, 8 mm×100 mm, elution with 0.1%H$_3$PO$_4$, 1%MeOH/H$_2$O) of the residue shows a mixture comprising 58.8% of the title compound.

[α]$_{589}$=–36.8° (c=5.0, H$_2$O)

Mass spectrum: m/z=278 (M+1)

IR (KBr): 1100, 1740, 2920, 3410 cm$^{-1}$ $^1$H NMR (dioxane-d$_8$): δ3.46 (dd,1H), 3.03 (t,1H), 2.85 (dd, 1H), 1.25–2.03 (m, 12H), 0.88–1.01 (m, 1H).

$^{13}$H NMR (dioxane-d$_8$): δ176.2, 55.1, 43.2, 37.5, 34.5, 33.5, 33.4, 31.4, 29.1, 28.5.

Analysis calculated for $C_{11}H_{20}NO_5P \cdot \frac{1}{2}H_2O$: C, 46.15; H, 7.39; N, 4.89. Found: C, 46.12; H, 6.99; N, 5.08.

We claim:

1. A process for preparing a compound of the formula

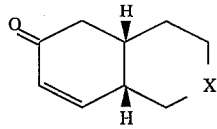

I wherein

X is $NR^1$; and $R^1$ is hydrogen, $C_1-C_6$ alkyl, arylalkyl, acyl, $C_1-C_6$ alkylsulfonyl, arylsulfonyl, alkoxycarbonyl, aryloxycarbonyl, or arylalkoxycarbonyl;

which comprises reacting a compound of the formula

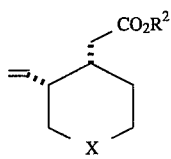

II wherein X is as defined above; and $R^2$ is hydrogen, t-butyl, $(C_1-C_6$ alkyl$)_3$silyl, methoxyethoxymethyl, methoxymethyl, tetrahydrofuran-2-yl, tetrahydropyran-2-yl, arylalkyl, cinnamyl, or allyl; with sulfuric acid.

2. The process of claim 1 wherein $R^1$ is alkoxycarbonyl.

3. The process of claim 1 wherein $R^2$ is t-butyl.

4. The process of claim 2 wherein $R^1$ is methoxycarbonyl and $R^2$ is t-butyl.

5. The process of claim 1 wherein the reaction is carried out at a temperature of about 0° C. to about 20° C.

6. The process of claim 1, wherein the reaction is carried out in concentrated sulfuric acid.

7. The process of claim 1, wherein $R^1$ is alkoxycarbonyl, $R^2$ is t-butyl and

* * * * *

UNITED STATES PATENT AND TRADEMARK OFFICE
CERTIFICATE OF CORRECTION

PATENT NO. : 5,461,156
DATED : October 24, 1995
INVENTOR(S) : Khau et al

It is certified that error appears in the above-indentified patent and that said Letters Patent is hereby corrected as shown below:

Column 16, line 15    5,461,156 should be changed from "$R^2$ is t-butyl and" to "$R^2$ is t-butyl and the reaction is carried out in concentrated sulfuric acid at a temperature of about 0°C to about 20°C.

Signed and Sealed this

Twelfth Day of March, 1996

Attest:

BRUCE LEHMAN

*Attesting Officer*    Commissioner of Patents and Trademarks